United States Patent [19]
Bright et al.

[11] Patent Number: 6,136,997
[45] Date of Patent: Oct. 24, 2000

[54] PROCESS FOR THE FORMATION OF HYDROCARBYL BIS(HYDROCARBYL PHOSPHATE)

[75] Inventors: Danielle A. Bright, New City; Ronald L. Pirrelli, Hartsdale, both of N.Y.

[73] Assignee: Akzo Nobel NV, Arnhem, Netherlands

[21] Appl. No.: 08/332,671

[22] Filed: Nov. 1, 1994

[51] Int. Cl.[7] .................. C07F 9/09; C07F 9/12; C07F 9/11
[52] U.S. Cl. .................................................... 558/99
[58] Field of Search ...................................... 558/99

[56] References Cited

U.S. PATENT DOCUMENTS

| | | | |
|---|---|---|---|
| 3,254,973 | 6/1966 | Giammaria et al. | 44/69 |
| 3,642,959 | 2/1972 | Nichols | 558/99 X |
| 3,737,487 | 6/1973 | Nichols | 260/973 |
| 4,133,846 | 1/1979 | Albright | 260/928 |
| 4,343,732 | 8/1982 | Zama et al. | 524/114 |

FOREIGN PATENT DOCUMENTS

| | | | |
|---|---|---|---|
| 0485807 | 5/1992 | European Pat. Off. | C07F 9/12 |
| 0521628 | 1/1993 | European Pat. Off. | C07F 9/12 |

OTHER PUBLICATIONS

Derwent Patent Abstract No. 05192 J/49 (Abstract JP 57/174,331 of Oct. 27, 1982.

*Primary Examiner*—Michael G. Ambrose
*Attorney, Agent, or Firm*—Richard P. Fennelly

[57] ABSTRACT

A process for the synthesis of a hydrocarbyl bis (dihydrocarbyl phosphate), such as a hydrocarbyl bis(diaryl phosphate), comprises the reaction of an unstable hydrocarbyl-containing diol, such as an aromatic group-containing diol, with a dihydrocarbyl halophosphate, such as diphenyl chlorophosphate, in the presence of a Lewis acid catalyst, such as magnesium dichloride, in the additional presence of an effective amount (e.g., up to about 100% by weight of diol and halophosphate) of a liquid hydrocarbon, such as an aliphatic hydrocarbon, like heptane, or an aromatic hydrocarbon, such as toluene, to enhance the removal of hydrogen halide by-product and thereby increase the yield of hydrocarbyl bis(dihydrocarbyl phosphate).

12 Claims, No Drawings

PROCESS FOR THE FORMATION OF HYDROCARBYL BIS(HYDROCARBYL PHOSPHATE)

BACKGROUND OF THE INVENTION

Processes for the synthesis of a hydrocarbyl bis (dihydrocarbyl phosphate) by the reaction of a hydrocarbyl diol with a dihydrocarbyl halophosphate in the presence of a Lewis acid catalyst are known to the prior art. For example, U.S. Pat. No. 3,254,973 to J. J. Giammaria et al. illustrates such a general reaction and employs nitrogen gas to sparge the reaction medium and remove hydrogen chloride as by-product. U.S. Pat. No. 4,133,846 to J. A. Albright illustrates an analogous reaction but does not show the nitrogen sparge aspect. More recent U.S. Pat. No. 4,343,732 to T. Zama et al. shows the reaction of certain diols, phosphorus oxychloride, and certain alcohols and phenols, in the presence of aluminum chloride as a catalyst, indicates (at Col. 4, lines 21–22) that inert solvents, such as toluene and xylene, may be used, but demonstrates no advantage for the use of a solvent.

When the diol used in the aforementioned reaction is alkylene in character, such as neopentylglycol, the reaction mixture comprising the desired diphosphate compound will generally contain undesired cyclic by-product(s), such as of the formula

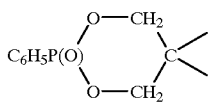

along with triphenyl phosphate, which lower the thermal stability of the diphosphate-containing compositions. If the diol which is used contains an alkylene group in association with phenyl moieties, such as in bisphenol A, the impurity will, for example, be isopropyl phenyl diphenyl phosphate. The unstable nature of such diols, in regard to the aforementioned formation of by-product(s), is due to either intramolecular reaction and rearrangement, such as in the case of the branched neopentyl glycol reagent and/or actual splitting apart of the diol molecule as in the case of bisphenol A which comprises two phenyl groups linked together with an alkylene moiety, namely —C(CH$_3$)$_2$—. The terminology "unstable hydrocarbyl-containing" will be used to characterize either type of such diols.

SUMMARY OF THE INVENTION

The present invention is a process for the synthesis of a hydrocarbyl bis(dihydrocarbyl phosphate), such as a hydrocarbyl bis(diaryl phosphate), which comprises the reaction of an unstable hydrocarbyl-containing diol, such as an alkylene- or alkylene bridged aromatic group-containing diol, with a dihydrocarbyl halophosphate, such as diphenyl chlorophosphate, in the presence of a Lewis acid catalyst, such as magnesium dichloride, in the additional presence of an effective amount (e.g., up to about 100% by weight of diol and halophosphate) of a liquid hydrocarbon, such as an aliphatic hydrocarbon, like heptane, to enhance the removal of hydrogen halide by-product and thereby increase the yield of hydrocarbyl bis(dihydrocarbyl phosphate) while reducing the formation of undesired cyclic by-products.

DETAILED DESCRIPTION OF THE INVENTION

The present process is one which is intended to synthesize a hydrocarbyl bisphosphate of the formula

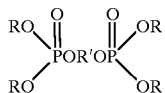

where R can be hydrocarbyl (such as, substituted or unsubstituted aryl) and R' can be either alkylene, such as derived from neopentyl glycol, or alkylene bridged arylene-containing, such as derived from bisphenol A.

The dihydrocarbyl halophosphate reactant used in the instant process has the formula

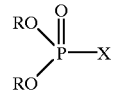

where R is hydrocarbyl (e.g., substituted or unsubstituted aryl) and X is halogen. Preferred compounds are the diarylchlorophosphates (e.g., diphenylchlorophosphate). This reactant is preferably present at about 2:1 (on a molar basis) to the following dihydroxy reaction.

The dihydroxy reactant (HOR'OH) is used to form the bridging group R' in the final compounds. The reaction is run at elevated temperature (above about 20° C.) but not at temperatures high enough to induce the formation of cyclic by-products and/or trihydrocarbyl phosphate using an effective amount (e.g., about 0.01% to about 1% by weight of the dihydrocarbylhalophosphate) of a Lewis acid catalyst. Such catalysts include such transition metal halides as magnesium chloride, aluminum chloride, zinc chloride, titanium tetrachloride and the like.

The present invention relies upon the presence of an additional amount of a liquid hydrocarbon, for example, an aliphatic hydrocarbon, such as heptane, or an aromatic solvent, such as toluene, to assist, as a "chaser", in driving off the hydrogen halide by-product. Generally speaking, the amount of solvent that is used will be up to about 100% by weight of the weight of diol and halophosphate, preferably up to about 50%, more preferably up to about 20%. The use of this liquid hydrocarbon allows for a high purity product to be formed at lower temperatures than possible if the liquid hydrocarbon were absent. The use of such lower temperature results in a lessened propensity for the formation of undesired by-products such as triphenyl phosphate and isopropenyl diphenyl phosphate in the case of bisphenol A and cyclic phosphates in the case of neopentyl glycol.

The present invention is illustrated by the Examples which follow.

EXAMPLE 1

Diphenyl chlorophosphate (0.5 mole), bisphenol A (0.25 mole), magnesium chloride ($2.63 \times 10^{-1}$ mole) and heptane (20 wt %) were heated to reflux (about 99° C.) for six hours. The disappearance of the hydroxy functionality was monitored by infrared analysis. Liquid chromatographic analysis (area %) of the reaction mixture showed the following composition: 1.5% triphenyl phosphate; 0.49% isopropenylphenyl diphenylphosphate; 1.7% bisphenol A diphenyl phosphate; 92.3% bisphenol A bis(diphenyl phosphate), which is referred to as "P$_2$" in the Table in Examples 2–5, below, and 2.4% of oligomeric bisphenol A bis(diphenyl phosphate) containing three phosphorus atoms.

EXAMPLES 2–5

In these Examples the effects of temperature, nitrogen sparge, and heptane concentration on the purity of the product described in Example 1 was determined (all amounts of product given in the following Table being on the basis of area percent, except for triphenyl phosphate, "TPP", which is based on weight percent):

| Example No. | Time (hrs) | Temp. (° C.) | Heptane (Wt %) | $N_2$ | A* | TPP | Half-Ester | $P_2$ |
|---|---|---|---|---|---|---|---|---|
| 2 | 6.5 | 115 | 10 | No | 2.5 | 1.5 | 0.79 | 91.2 |
| 3 | 5 | 130 | 0 | No | 14.7 | 3.5 | 3.1 | 65.9 |
| 4 | 13 | 120 | 0 | Yes | 8.5 | 1.9 | 0.42 | 84.7 |
| 5 | 5.5 | 150 | 0 | No | 9.6 | 4.3 | 0.27 | 70.6 |

* = "A" is used to identify the isopropenylphenyl diphenylphosphate component.

EXAMPLES 6–10

Neopentyl glycol bis(diphenylphosphate) was made by heating to reflux 1.1 moles (295.5 grams) of diphenylchlorophosphate, 0.5 mole (52.0 grams) of neopentyl glycol, 0.2 gram of magnesium chloride, and 100 ml of a non-polar solvent. Upon reaction completion, the solvent was recovered by vacuum stripping, and the reaction mixture was washed with 2% sulfuric acid aqueous solution, 2% sodium hydroxide aqueous solution, and water. After removal of traces of water the following results were obtained:

| Run No. | Solvent | Rxn. Temp. (° C.) | Rxn. Time (hrs) | Yield (%) |
|---|---|---|---|---|
| 6 | Hexane | 70 | 20 | 94 |
| 7 | Heptane | 95 | 17 | 92 |
| 8 | Isoparaffin* | 115 | 11 | 90 |
| 9 | Isoparaffin* | 130 | 11 | 93 |
| 10 | Xylene | 140 | 8 | 95 |
| 11 | None | 100 | 17 | 85 |

*ISOPAR E brand from Exxon Company. In Run No. 9, 50 ml of this solvent was used rather than 100 ml as in Run No. 10.

| | High Pressure Liquid Chromatography Analysis | | |
|---|---|---|---|
| Run No. | Bisphosphate (Area %) | Triphenyl Phosphate (Wt %) | Cyclic By-product (Area %) |
| 6 | 96.3 | 1.4 | 1.1 |
| 7 | 93.1 | 1.3 | 2.5 |
| 8 | 96.7 | 1.2 | 1.4 |
| 9 | 76.3 | 15.2 | 3.0 |
| 10 | 62.5 | 18.9 | 7.4 |
| 11 | 88.6 | 6.2 | 2.2 |

EXAMPLE 12

Dibromoneopentyl glycol bis(diphenylphosphate) was made by heating to ref lux (117° C.) about 1.1 moles (295.5 grams) of diphenylchlorophosphate, about 0.5 mole (131.0 grams) of dibromoneopentyl glycol, 0.2 grams of magnesium chloride, and 100 ml of ISOPAR E isoparaffin solvent. After fifteen hours at this temperature, the solvent was removed by layer separation. The reaction mixture was washed as described in Examples 6–10. There was left 348 grams of an oil (96% yield) that assayed at 81.5 area % of the desired product by high pressure liquid chromatography. The by-products were triphenylphosphate (8.2% by weight) and cyclic phosphorinane (2.6 area %)

The foregoing Examples have been presented to illustrate certain preferred embodiments of the present invention and, for that reason, should not be construed in a limiting sense. The scope of protection sought is set forth in the Claims which follow.

We claim:

1. In a process for the synthesis of a hydrocarbyl bis (dihydrocarbyl phosphate) which comprises the reaction of an unstable hydrocarbyl-containing diol with a dihydrocarbyl halophosphate in the presence of a Lewis acid catalyst, wherein the improvement comprises the additional presence of an effective amount of a liquid hydrocarbon to enhance the removal of hydrogen halide by-product and decrease the reaction temperature while increasing the yield and purity of hydrocarbyl bis(dihydrocarbyl phosphate).

2. A process as claimed in claim 1 wherein the hydrocarbyl bis(dihydrocarbyl phosphate) is a hydrocarbyl bis(diaryl phosphate).

3. A process as claimed in claim 1 wherein the hydrocarbyl diol is selected from the group consisting of an alkylene group-containing diol and an alkylene bridged aromatic group-containing diol.

4. A process as claimed in claim 1 wherein the hydrocarbyl bis(dihydrocarbyl phosphate) is a hydrocarbyl bis(diaryl phosphate) and the hydrocarbyl diol is an alkylene group-containing diol.

5. A process as claimed in claim 1 wherein the hydrocarbyl bis(dihydrocarbyl phosphate) is a hydrocarbyl bis(diaryl phosphate) and the hydrocarbyl diol is an alkylene bridged aromatic group-containing diol.

6. A process as claimed in claim 1 wherein the Lewis acid catalyst is magnesium dichloride.

7. A process as claimed in claim 1 wherein the hydrocarbyl bis(dihydrocarbyl phosphate) is a hydrocarbyl bis(diaryl phosphate), the hydrocarbyl diol is selected from the group consisting of an alkylene group-containing diol and an alkylene bridged aromatic group-containing diol, and the Lewis acid catalyst is magnesium dichloride.

8. A process as claimed in claim 1 wherein the liquid hydrocarbon is an aliphatic hydrocarbon.

9. A process as claimed in claim 1 wherein the hydrocarbyl bis(dihydrocarbyl phosphate) is a hydrocarbyl bis(diaryl phosphate), the hydrocarbyl diol is selected from the group consisting of an alkylene group-containing diol and an alkylene bridged aromatic group-containing diol, the Lewis acid catalyst is magnesium dichloride, and the liquid hydrocarbon is an aliphatic hydrocarbon.

10. A process as claimed in claim 1 wherein the liquid hydrocarbon is present at up to about 50% of the weight of diol and halophosphate.

11. A process as claimed in claim 9 wherein the liquid hydrocarbon is present at up to about 50% of the weight of diol and halophosphate.

12. A process as claimed in claim 1 wherein the hydrocarbyl bis(dihydrocarbyl phosphate) is a hydrocarbyl bis (diaryl phosphate), the hydrocarbyl diol is selected from the group consisting of an alkylene group-containing diol and an alkylene bridged aromatic group-containing diol, the Lewis acid catalyst is magnesium dichloride, the liquid hydrocarbon is an aliphatic hydrocarbon, and the process is performed at a temperature of above about 20° C.

* * * * *